United States Patent
Roth et al.

(10) Patent No.: US 8,551,093 B2
(45) Date of Patent: Oct. 8, 2013

(54) BONE FIXATION SYSTEM

(75) Inventors: Christoph Andreas Roth, West Chester, PA (US); Harry T. Hall, IV, Downingtown, PA (US)

(73) Assignee: Depuy Synthes Products, LLC, Raynham, MA (US)

( * ) Notice: Subject to any disclaimer, the term of this patent is extended or adjusted under 35 U.S.C. 154(b) by 708 days.

(21) Appl. No.: 10/992,261

(22) Filed: Nov. 18, 2004

(65) Prior Publication Data

US 2005/0070903 A1 Mar. 31, 2005

Related U.S. Application Data

(63) Continuation of application No. 09/978,002, filed on Oct. 17, 2001, now Pat. No. 6,835,197.

(51) Int. Cl.
*A61B 17/56* (2006.01)

(52) U.S. Cl.
USPC .......................................................... 606/64

(58) Field of Classification Search
USPC .............. 606/60, 62, 64–67, 72, 73, 300–331
See application file for complete search history.

(56) References Cited

U.S. PATENT DOCUMENTS

| | | | | |
|---|---|---|---|---|
| 4,612,920 A * | 9/1986 | Lower | ............................. | 606/66 |
| 4,657,001 A * | 4/1987 | Fixel | ................................ | 606/66 |
| 5,032,125 A * | 7/1991 | Durham et al. | ................. | 606/62 |
| 5,176,681 A * | 1/1993 | Lawes et al. | .................... | 606/64 |
| 5,312,406 A * | 5/1994 | Brumfield | ........................ | 606/64 |
| 5,458,600 A * | 10/1995 | Stapert et al. | ................... | 606/63 |
| 5,489,284 A * | 2/1996 | James et al. | .................... | 606/62 |
| 5,658,288 A * | 8/1997 | Kim | | |
| 5,741,256 A | 4/1998 | Bresina | | |
| 5,766,174 A * | 6/1998 | Perry | ............................. | 606/62 |
| 5,779,705 A * | 7/1998 | Matthews | ........................ | 606/67 |
| 5,908,422 A * | 6/1999 | Bresina | ............................ | 606/67 |
| 5,976,139 A * | 11/1999 | Bramlet | .......................... | 606/66 |
| 6,059,785 A | 5/2000 | Schavan et al. | | |
| 6,187,007 B1 * | 2/2001 | Frigg et al. | ..................... | 606/72 |
| 6,221,074 B1 * | 4/2001 | Cole et al. | ...................... | 606/62 |
| 6,235,031 B1 * | 5/2001 | Hodgeman et al. | ............ | 606/64 |
| 6,319,253 B1 * | 11/2001 | Ackeret et al. | .................. | 606/64 |
| 6,406,477 B1 * | 6/2002 | Fujiwara | ......................... | 606/67 |
| 6,409,730 B1 * | 6/2002 | Green et al. | .................... | 606/72 |
| 6,743,233 B1 * | 6/2004 | Baldwin et al. | ................. | 606/73 |

* cited by examiner

*Primary Examiner* — Mary Hoffman

(74) *Attorney, Agent, or Firm* — Fay Kaplun & Marcin, LLP

(57) ABSTRACT

An implant for fixation of a bone includes a shaft having a proximal end and a distal end, and a longitudinal axis defined between the proximal end and the distal end. A plurality of blades are disposed on the shaft, and are helically twisted about the longitudinal axis. At least one of the blades has a variable blade width that increases in a direction along the longitudinal axis. A mechanism for coupling the implant to a second fracture fixation implant may be provided separately or in combination.

25 Claims, 12 Drawing Sheets

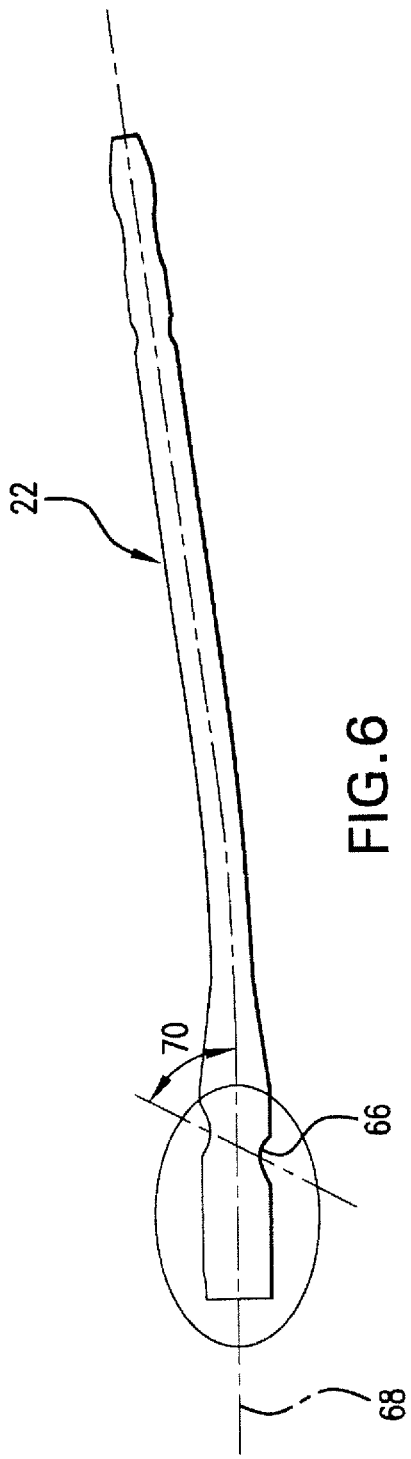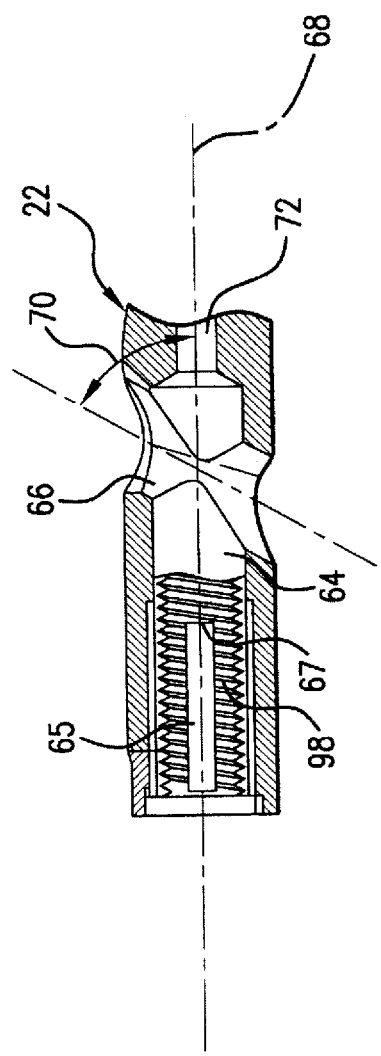

BONE FIXATION SYSTEM

CROSS-REFERENCE TO RELATED APPLICATIONS

The present application is a Continuation Application of U.S. patent application Ser. No. 09/978,002, filed Oct. 17, 2001 now U.S. Pat. No. 6,835,197, the contents of which are incorporated by reference herein.

FIELD OF THE INVENTION

The present invention relates generally to a system for fixation of two or more parts of a fractured bone. More specifically, the present invention relates to a bone implant and locking apparatus for internal fixation of a long bone, such as a femur.

BACKGROUND OF THE INVENTION

Fractures commonly occur in the femur, and especially in the femoral neck and intertrochanteric regions. Traditionally, these fractures have been treated using a nail located in the femoral head in cooperation with a side plate located on the outside of the femur, or in cooperation with an intramedullary nail located in the intramedullary canal. The nail cooperates with the side plate or intramedullary nail to align and compress the bone fragments.

A high incidence of death is associated with hip fractures due to the injury itself or related complications. Frequent complications may arise when two or more bone fragments are forced towards each other when the patient supports his or her weight on the healing bone. For example, a sharp implanted nail or hip screw may cut through and penetrate the femoral head or neck; or a nail, hip screw, side plate, or intramedullary nail may bend or break under load where the contact between bone fragments is insufficient for the bone itself to carry the patient's weight.

A variety of compressible fixation systems have been developed to maximize bone to bone contact while permitting bone fragments to migrate towards one another. For example, helical blades have been developed that may be inserted into and secured to the neck of a femur, and coupling mechanisms have been developed to slidably couple the helical blade to a side plate or intramedullary nail.

The prior art blades, however, may be susceptible to migration within the bone fragment and, even worse, may break free or pull out of the bone fragments, thus allowing the bone fragments to separate and/or become misaligned. Prior art blades are also susceptible to bending stresses, which may lead to undesirable bending or breakage of the blade.

In addition, many prior art coupling mechanisms provide unlimited amounts of sliding between the blade and the side plate or intramedullary nail, which may lead to disassembly of the blade and side plate/intramedullary nail. Furthermore, prior art coupling mechanism are often complicated and difficult to assemble during implantation.

Thus, a need exists for improved bone fixation systems.

SUMMARY OF THE INVENTION

The present invention is directed to bone fixation system including implants and coupling mechanisms for fixation of a bone. According to one aspect of the invention, an implant for fixation of a bone includes a shaft having proximal and distal ends and defines a longitudinal axis between the proximal and distal ends. A plurality of blades, each having proximal and distal ends, are disposed on the shaft and are helically twisted about the longitudinal axis. According to one embodiment, the plurality of blades may twist about 90° around the longitudinal axis. At least one of the blades may have a variable blade width that varies along the longitudinal axis. For example, the variable blade width may increase in a direction from the blade proximal end toward the blade distal end. Additionally or alternatively, at least one of the blades may have a variable blade height that varies along the longitudinal axis. For example, the variable blade height may increase in a direction from the blade proximal end toward the blade distal end. The variable blade height is preferably substantially zero at the blade proximal end, such that the proximal end of the blade is substantially flush with the proximal end of the shaft.

According to a further aspect of the invention, the shaft of the implant may define a bladed portion and a non-bladed portion. The non-bladed portion may define a non-bladed diameter, and the bladed portion may define a bladed diameter that is smaller than the non-bladed diameter. In addition, the non-bladed portion may include a tapered region located substantially adjacent the bladed portion, wherein the tapered region defines a tapered region diameter that decreases in a direction toward the bladed portion. The tapered region may further define a neck diameter at a point substantially adjacent the blades that is smaller than the blade diameter.

The present invention is also directed to a coupling mechanism for coupling a first fracture fixation implant to a second fracture fixation implant. The coupling mechanism includes a body member receivable in the first implant and including a single prong extending from the body for contacting a surface of the second implant. The coupling mechanism further includes a drive member rotatably coupled to the body member for threadable engagement with the first implant. The drive member rotates freely with respect to the body member and may be used to urge the body member toward the second implant such that the single prong contacts the surface of the second implant and substantially prevents rotation of the second implant with respect to the first implant. More specifically, the single prong may define a first engagement surface, the second implant may define a second engagement surface, and the first and second engagement surfaces may interact to substantially prevent rotation of the second implant with respect to the first implant.

According to a further aspect of the invention, the single prong may limit sliding of the second implant with respect to the first implant. For example, the second engagement surface may include stops formed adjacent at least one of its ends for contacting the prong to prevent further sliding of the second implant.

The coupling mechanism may also be provided in a system for fixation of a fractured bone, which includes first and second fracture fixation implants.

BRIEF DESCRIPTION OF THE DRAWINGS

The detailed description will be better understood in conjunction with the accompanying drawings, wherein like reference characters represent like elements, as follows:

FIG. 6 is a right side view of the second implant of FIG. 5;

FIG. 7 is an enlarged, cross-sectional view of a portion of the second implant of FIG. 5;

DETAILED DESCRIPTION OF THE PREFERRED EMBODIMENTS

Figure 1:
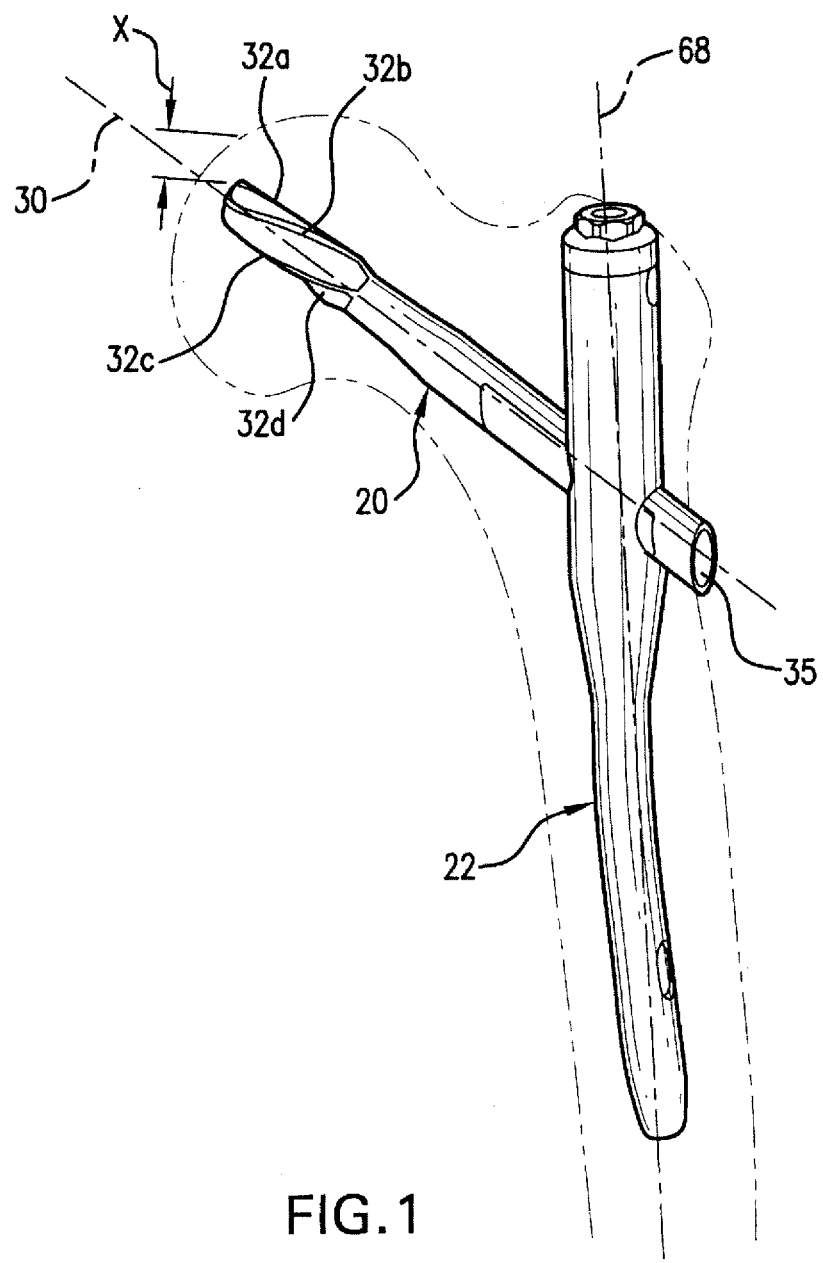
FIG. 1 is a perspective view of one illustrative embodiment of a fracture fixation system according to the present invention, shown implanted in a femur.

Referring to FIG. 1, a fracture fixation implant 20 according to one embodiment of the present invention is shown implanted in a femur and coupled to a second fracture fixation implant 22, which is shown for illustrative purposes as an intramedullary nail 22. Implant 20 may be used in conjunction with an intramedullary nail 22 or other fracture fixation member to treat orthopaedic trauma, impending bone fractures, and bone fractures. For example, implant 20 may be used to treat intertrochanteric fractures of the femur. Implant 20 is not limited to use in conjunction with an intramedullary nail 22, however, and may be used alone or in conjunction with any number of implants, bone plates, etc., known to one of ordinary skill in the art. Furthermore, the present invention is not limited to treatment of the femur, and may be used to treat any of the bones in the human and/or animal bodies.

Figure 2:
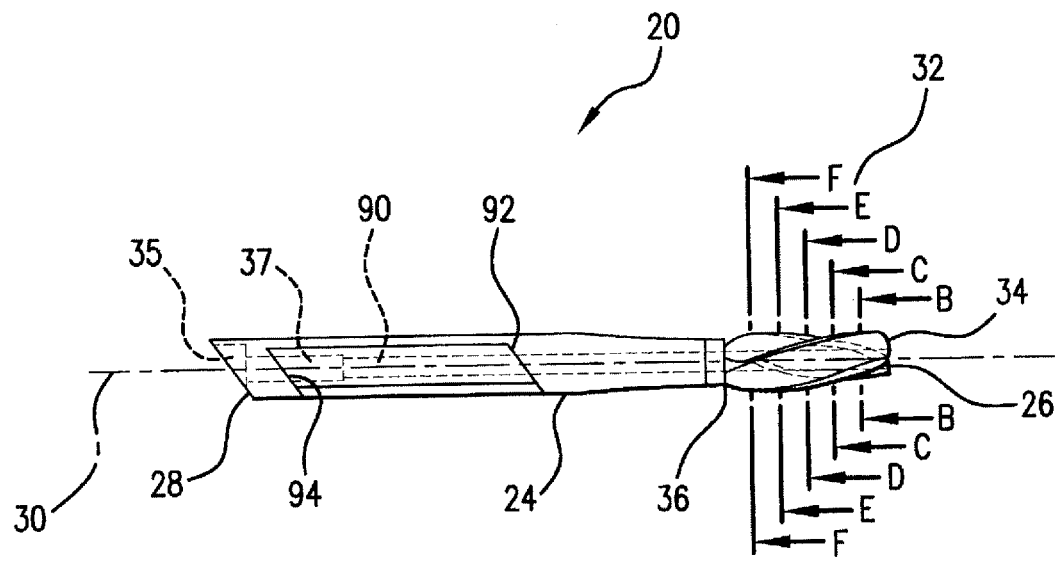
FIG. 2 is a left side view of an illustrative embodiment of a fracture fixation implant of FIG. 1.
Figure 3:
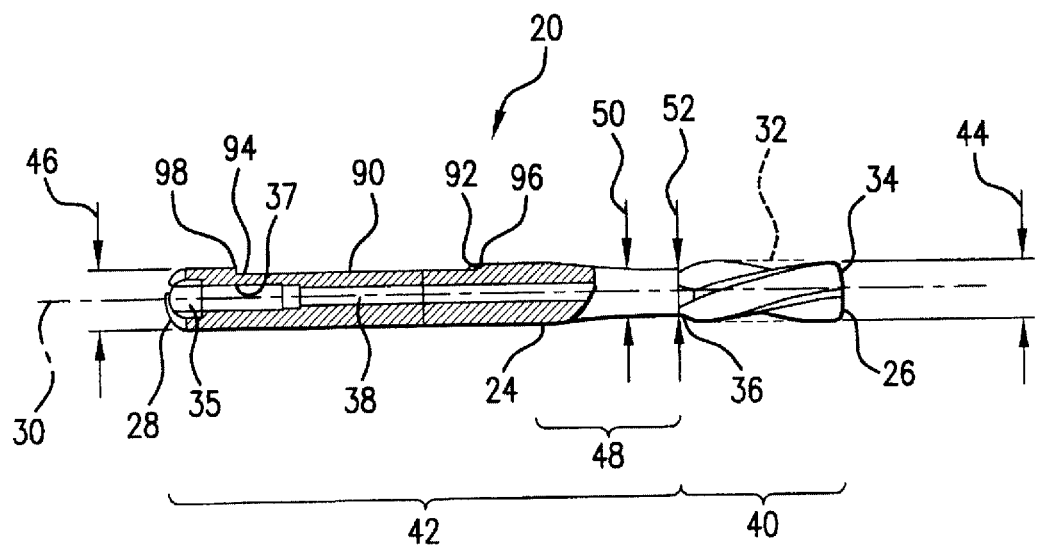
FIG. 3 is a top view of the implant of FIG. 2, with portions shown in cross-section.

Referring to FIGS. 2 and 3, implant 20 includes a shaft 24 having a proximal end 26 and a distal end 28, and defines a longitudinal axis 30 between the proximal and distal ends 26, 28. A plurality of blades 32 are disposed on shaft 24 and are helically twisted about longitudinal axis 30, as will be discussed in more detail below. The plurality of blades 32 has a proximal end 34 and a distal end 36, and blade proximal end 34 is preferably located substantially adjacent shaft proximal end 26. Blades 32 may alternatively be located on shaft 24 at an intermediate position between shaft proximal and distal ends 26, 28.

A cannulation 38 (shown in FIG. 3) may optionally be provided in shaft 24 and oriented substantially coaxially with longitudinal axis 30. If provided, cannulation 38 may be sized to permit insertion of a guide wire (not shown) to aid in the alignment of implant 20 during the implantation procedure, as is commonly known in the art. Shaft distal end 28 may be configured and dimensioned for attachment to an insertion device (not shown), such as an insertion handle or driving cap. For example, as shown in FIGS. 2 and 3, shaft distal end 28 may be angled with respect to shaft longitudinal axis 30 and/or include a recess 35 having a threaded portion 37 for attachment to an insertion device. As best seen in FIG. 1, recess 35 may have a non-symmetrical shape, such as a D-shape, so that the rotational orientation of implant 20 can be readily ascertained from distal end 28.

Referring to FIGS. 4A-4F, implant 20 is preferably provided with four helical blades 32a-32d that twist about longitudinal axis 30. One of ordinary skill in the art will know and appreciate, however, that implant 20 may be provided with any number of blades 32, such as five, six, or eight blades. Blades 32a-32d each have a helical twist about longitudinal axis 30, which is shown as approximately 90°. Thus, each blade is rotated approximately 90° about longitudinal axis between proximal end 34 (shown in FIG. 4A) and distal end 36 (shown in FIG. 4F). The helical twist is such that once implant 20 is driven into a bone, e.g., the femur, the helical twist of blades 32 substantially prevents implant 20 from sliding in the bone along longitudinal axis 30. One of ordinary skill in the art will know and appreciate that blades 32 may have any amount of helical twist about longitudinal axis 30, such as, for example, 45°, 60°, 120°, 180°, 360°, 720°, or 1080°.

As shown in FIGS. 4A-4F, a first blade 32a and a second blade 32c are substantially diametrically opposed from one another about longitudinal axis 30, and a third blade 32b and a fourth blade 32d are also substantially diametrically opposed from one another about longitudinal axis 30. First and second blades 32a, 32c are preferably about 90° out of phase with respect to third and fourth blades 32b, 32d, however other configurations are within the present invention. Preferably in one embodiment, at least one of the blades 32 defines a blade width W that varies along longitudinal axis 30. More specifically, blade 32b has a blade width $W_b$ that increases from blade proximal end 34 (shown in FIG. 4A) to blade distal end 36 (shown in FIG. 4F), such that blade width $W_b$ is greatest substantially adjacent blade distal end 36 and smallest substantially adjacent blade proximal end 34. Preferably, blade width $W_b$ gradually tapers outward from proximal end 34 to distal end 36.

In the illustrative embodiment shown, blades 32b and 32d both have variable blade widths $W_b$ and $W_d$, respectively. When implant 20 is in the intended rotational orientation within the bone, shown in FIG. 1, the distal ends 36 of blades 32b and 32d are substantially aligned with the plane in which the majority of forces are applied to implant 20 (a substantially vertical plane, in the view of FIG. 1, extending through longitudinal axis 30 and longitudinal axis 68). Thus, the greater widths $W_b$, $W_d$ of blades 32b, 32d around distal ends 36 increase the bending strength of implant 20, while the decreased widths at proximal ends 34 provides for ease of insertion of implant 20 into the bone. The taper of blades 32b and 32d also helps to prevent sliding of implant 20 within the bone along longitudinal axis 30.

Additionally or alternatively, one or more of the blades 32 may have a substantially constant blade width W. For example, as shown in FIGS. 4A-F, blade 32c may have a substantially constant width $W_c$ that is substantially equal at blade proximal end 34 (shown in FIG. 4A), at the intermediate points shown in FIGS. 4B-4E, and at blade distal end 36 (shown in FIG. 4F). In the illustrative embodiment shown, blade 32a also has a substantially constant blade width $W_a$ (blade width $W_a$ appears to vary in FIGS. 4A-4F due to the variance in blade height $H_a$, discussed below, however blade width $W_a$ is actually substantially constant along longitudinal axis 30).

Figure 4A:
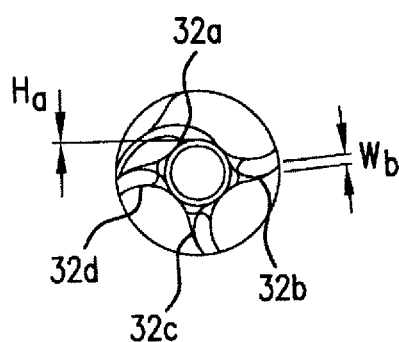
FIG. 4A is a front view of the implant of FIG. 2.
Figure 4B:
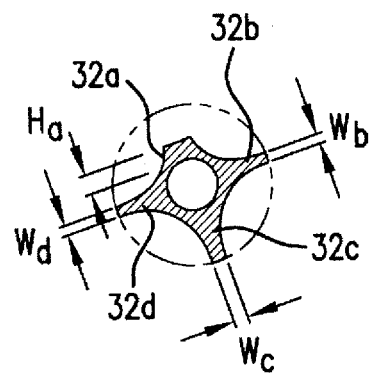
FIGS. 4B to 4F are cross-sectional views of the implant of FIG. 2, taken along lines B-B to F-F of FIG. 2, respectively.
Figure 4C:
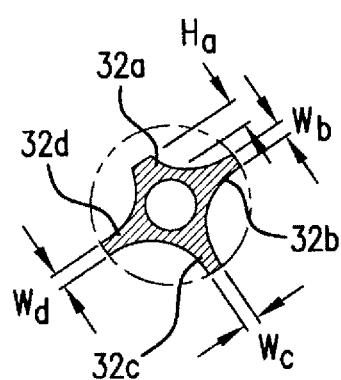
Figure 4D:
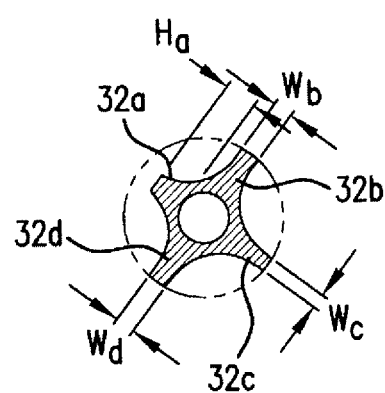
Figure 4E:
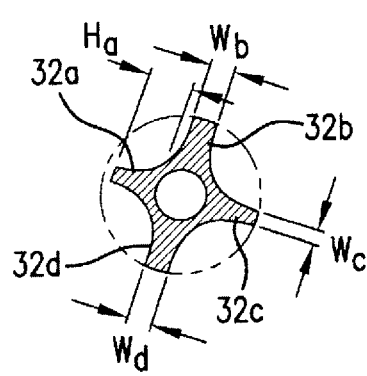
Figure 4F:
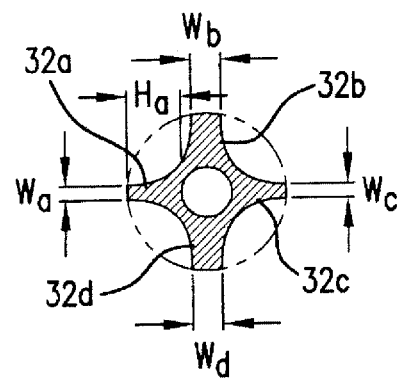

According to a further aspect of the present invention, at least one of the blades 32 may define a blade height H (defined perpendicularly to longitudinal axis 30 from the base of the blade 32 to the tip of the blade) that varies along longitudinal axis 30. In particular, blade 32a may have a blade height $H_a$ that increases from blade proximal end 34 (shown in FIG. 4A) to blade distal end 36 (shown in FIG. 4F), such that blade height $H_a$ is greatest substantially adjacent blade distal end 36 and smallest substantially adjacent blade proximal end 34. Preferably, blade height $H_a$ is substantially zero at blade proximal end 34, as shown in FIG. 4A, such that blade 32a is substantially flush with shaft 24 at proximal end 34. When implant 20 is in the intended rotational orientation of FIG. 1, the decreased height $H_a$ or substantially flush configuration of blade 32a at proximal end 34 increases the distance X implant 20 must migrate in the bone before it cuts completely through the bone. Also, the flush configuration of blade 32a at proximal end 34 reduces migration of implant 20 in the bone (because there is virtually no blade 32a at proximal end 34 to cut through the bone when a load is applied).

Additionally or alternatively, at least one of the blades 32 may have a substantially constant blade height H. For example, as shown in FIGS. 4A-4F, blades 32b, 32c, and 32d each have substantially constant blade heights $H_b$, $H_c$, and $H_d$, respectively, that are substantially constant from blade proximal end 34 (shown in FIG. 4A) through the intermediate points shown in FIGS. 4B-4E, and at blade distal end 36 (shown in FIG. 4F).

Referring back to FIG. 3, implant 20 includes a bladed portion 40, upon which blades 32 are disposed, and a non-bladed portion 42 that is without any blades 32. Bladed portion 40 defines a bladed diameter 44 and non-bladed portion 42 defines a non-bladed diameter 46. The maximum diameter of bladed portion 40 (i.e., where bladed diameter 44 is at its greatest) may preferably be smaller than the maximum diameter of non-bladed portion 42 (i.e., where non-bladed diameter 46 is at its greatest). According to this configuration of implant 20, bladed portion 40 may pass freely through bore 66 in intramedullary nail 22 (shown in FIG. 5 and discussed in detail below) to provide ease of assembly, and non-bladed portion 42 may mate with bore 66 to provide a stable sliding interconnection between non-bladed portion 42 and bore 66.

Non-bladed portion 42 may be further provided with a tapered region 48 located substantially adjacent the bladed portion 40. Tapered region 48 defines a tapered region diameter 50 that decreases in a direction toward bladed portion 40. For example, tapered region diameter 50 may, at the location adjacent to the untapered region, be equal to non-bladed diameter 46 and decrease, or taper inward, along longitudinal axis 30 towards the distal end of bladed portion 40. Preferably, tapered region 48 is curved inwardly to provide even stress distribution throughout the tapered region 48, and to provide a uniform bending of implant 20 under loading. Additionally or alternatively, tapered region 50 may further define a neck diameter 52 at a point substantially adjacent bladed portion 40 (at the point where non-bladed portion 42 meets bladed portion 40) that is smaller than bladed diameter 44. This configuration of implant 20 provides for bone ingrowth between the non-bladed portion 42 and the bladed portion 40, thereby providing resistance against implant 20 from backing out of the bone. In addition, tapered region 48 serves to self-center implant 20 as implant 20 is inserted into bore 66 of intramedullary nail 22 (shown in FIG. 5).

The present invention is also directed to a mechanism which may be used to couple a first fracture fixation implant 20 to a second fracture fixation implant 22. As described herein, the coupling mechanism may be used to couple implant 20, described above, to an intramedullary nail 22. The coupling mechanism, however, is not limited to use with implant 20 and/or intramedullary nail 22, and may be used to couple any number of different fracture fixation implants known to those of ordinary skill in the art.

Figure 5:
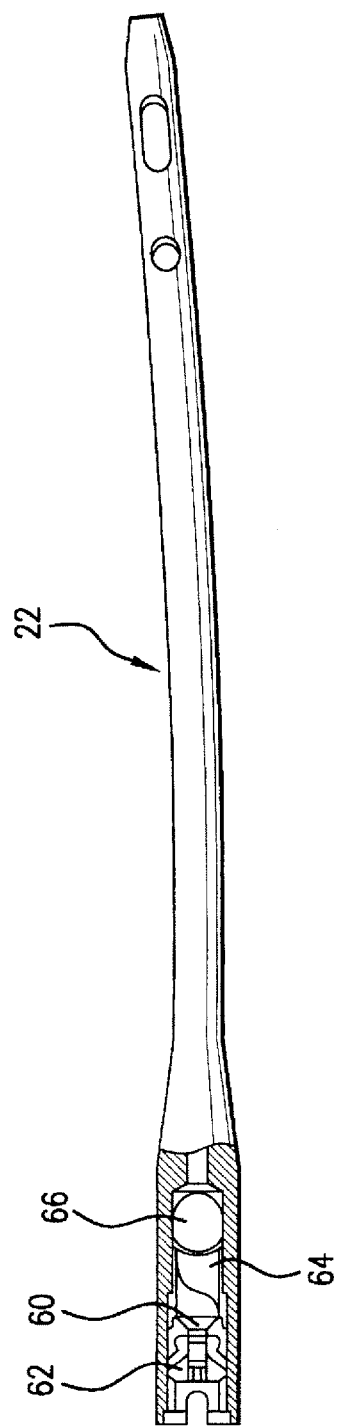
FIG. 5 is a right side view of an illustrative embodiment of a coupling mechanism according to the present invention, shown inside the second fracture fixation implant of FIG. 1.

Referring to FIG. 5, a body member 60 and a drive member 62 are shown assembled into an interior channel 64 in intramedullary nail 22. Body member 60 and drive member 62 cooperate with channel 64 to secure implant 20 (not shown) in a bore 66 that extends through intramedullary nail 22. As will be discussed in more detail below, body member 60, drive member 62 and channel 64 cooperate to substantially prevent implant 20 from rotating about its longitudinal axis 30 (shown in FIGS. 1-3) within bore 66, and also to limit sliding of implant 20 within bore 66 to a predetermined distance.

Referring to FIGS. 6 and 7, the configuration of intramedullary nail 22 is shown in detail. Intramedullary nail 22 defines a longitudinal axis 68 that may be straight, bent (shown), curved, or otherwise configured and dimensioned to mate with the geometry of the bone into which intramedullary nail 22 is to be implanted. Channel 64 extends substantially along longitudinal axis 68, and is dimensioned and configured to receive body member 60 and drive member 62, such that the two parts may move in channel 64 at least partially along longitudinal axis 68. A series of threads 98 may be disposed on channel 64, as will be discussed in detail below. Also, a pair of grooves 65 may be formed on channel 64, and are preferably diametrically opposed from one another.

Still referring to FIGS. 6 and 7, bore 66 extends through intramedullary nail 22 and intersects with channel 64, and is dimensioned and configured to allow implant 20 to slide therethrough. According to the illustrative embodiment shown, bore 66 is configured and dimensioned to slidably engage non-bladed portion 42 of implant 20, and maintain implant 20 in angular relationship with respect to longitudinal axis 68. As shown, bore 66 is disposed at an angle 70 with respect to longitudinal axis 68. Angle 70 may be selected to match the anatomy of the patient in which intramedullary nail 22 and implant 20 are to be implanted, for example, to correspond to the femoral neck/shaft angle of a human patient. A cannulation 72 (partially shown in FIG. 7) may optionally be provided through intramedullary nail 22 in substantial coaxial alignment with longitudinal axis 68. If provided, cannulation 72 may be sized to permit insertion of a guide wire (not shown) to guide the implantation of intramedullary nail 22 into the bone, as is commonly known in the art.

Referring to FIGS. 8-11, body member 60 is shown in detail. Body member 60 includes a substantially cylindrical portion 78 that defines a longitudinal axis 80 of the body member 60, and a prong 76 extending from cylindrical portion 78. One of ordinary skill in the art will know and appreciate, however, that body member 60 is not limited to the shape shown, and may have any shape that permits body member 60 to move within channel 64 of intramedullary nail 22. A pair of alignment tabs 85 (shown in FIGS. 8 and 11) may extend from cylindrical portion 78. If provided, tabs 85 are positioned on body member 60 such that tabs 85 may be received in grooves 65 (shown in FIG. 7) of intramedullary nail 22. Cooperation between tabs 85 and grooves 65 substantially limits rotation of body member 60 within channel 64 of intramedullary nail 22.

Cooperation between tabs 85 and grooves 65 also maintains surface 79 (illustrated in FIG. 9) of body member 60 at a distance from implant 20 when the coupling mechanism is assembled and locked, thus allowing implant 20 to freely slide in bore 66. More specifically, grooves 65 have ends 67 (shown in FIG. 7) that contact tabs 85 and prevent body member 60 from sliding any further towards bore 66. Ends 67 are located in channel 64 at locations such that tabs 85 contact ends 67 (to prevent further movement of body member 60 towards bore 66) before surface 79 contacts implant 20. As shown in the figures, surface 79 is preferably oriented at an angle 81 with respect to longitudinal axis 80 that is substantially equal to angle 70, although angle 81 may be different than angle 70. According to the configuration where angle 81 is substantially equal to angle 70, angled surface 79 remains at a constant distance from implant 20 when the coupling mechanism is assembled and locked.

Figure 8:
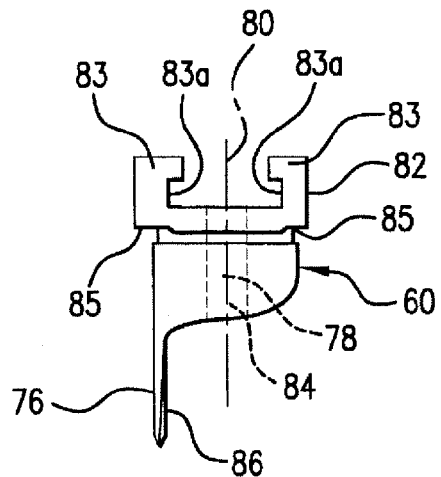
FIG. 8 is a front view of a body member of the coupling mechanism of FIG. 5.
Figure 9:
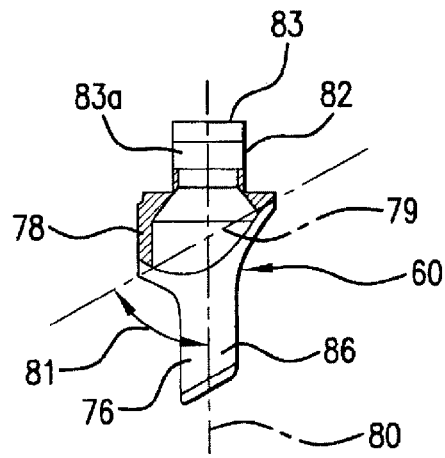
FIG. 9 is a left side view of the body member of FIG. 8, with portions shown in cross-section.
Figure 10:
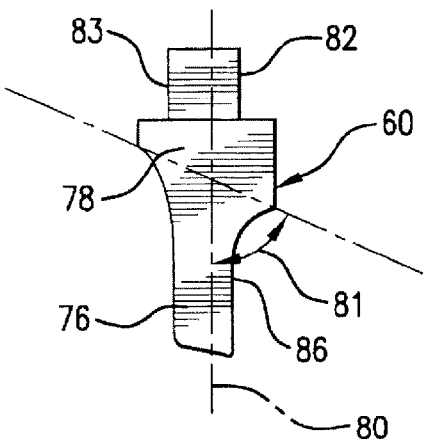
FIG. 10 is a right side view of the body member of FIG. 8.
Figure 11:
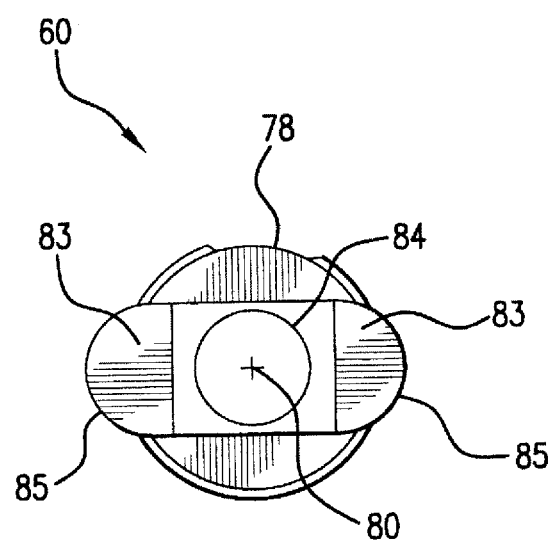
FIG. 11 is a top view of the body member of FIG. 8.

Body member 60 may also include an attachment portion 82, which is configured and dimensioned to rotatably couple body member 60 to drive member 62, as will be discussed in more detail below. As shown in FIG. 8, attachment portion 82 includes a pair of upward-extending arms 83 that define a pair of opposed channels 83a for receiving a portion of drive member 62 therein. A cannulation 84 may optionally be provided through body member 60 in substantial coaxial alignment with longitudinal axis 80 to permit insertion of a guide wire (not shown) therethrough.

Still referring to FIGS. 8-11, prong 76 extends away from body member 60 in a direction substantially parallel to longitudinal axis 80, and may be configured and dimensioned to contact implant 20 to limit sliding and rotation of implant 20 with respect to longitudinal axis 30 (shown in FIG. 1). As will be discussed in more detail below, prong 76 may be provided with a first engagement surface 86 that contacts a second engagement surface 90 formed on implant 20 to substantially prevent rotation of implant 20 and limit sliding of implant 20, as will be discussed in more detail below. According to alternative embodiments of the present invention, body member 60 may be provided with two or more prongs to contact two or more engagement surfaces formed on implant 20. For example, a second prong may extend from body member 60 in the same direction as prong 76, and may be diametrically opposed to prong 76 about longitudinal axis 80 and substantially parallel to prong 76. The two-pronged embodiment may be used, for example, with an implant 20 having two diametrically opposed engagement surfaces. Alternatively, a single-pronged embodiment may be used with an implant 20 having two or more engagement surfaces.

Referring back to FIGS. 2 and 3, an exemplary embodiment of second engagement surface 90 is shown formed on implant 20. According to the embodiment shown, second engagement surface 90 is substantially flat and extends along longitudinal axis 30. First and second stops 92, 94 may be located at opposite ends of locking second engagement surface 90. In the illustrative embodiment shown, second engagement surface 90 is recessed into shaft 24 of implant 20, and stops 92, 94 are formed at the boundaries of the recessed surface. One of ordinary skill in the art will know and appreciate, however, that other configurations of engagement surface 90 and stops 92, 94, are within the present invention. For example, engagement surface 90 and/or stops 92, 94 may alternatively be formed on or extend from shaft 24. Furthermore, as discussed above, implant 20 may alternatively be provided with two or more second engagement surfaces 90, which may interact with a body member 60 having one, two or more prongs.

When implant 20 is received in bore 66 in intramedullary nail 22 and body member 60 is located in channel 64 with tabs 85 bottomed out on ends 67 of groves 65, prong 76 interacts with implant 20 to substantially prevent rotation of implant 20 about its longitudinal axis 30. More specifically, prong 76 fits tightly in the space between channel 64 and implant 20 such that first and second engagement surfaces 86, 90 are maintained in contact under the constraints of channel 64. In this configuration, implant 20 is substantially prevented from rotation about its longitudinal axis 30 due to abutment of substantially flat first and second engagement surfaces 86, 90. The coupling mechanism may thus be used to maintain implant 20 in its intended rotational orientation within the bone. If provided, stops 92, 94 prevent implant 20 and implant 22 from coming apart, and may also limit the amount of sliding of implant 20 along its longitudinal axis 30 to the length of second engagement surface 90. For example, once implant 20 slides distally until first stop 92 contacts prong 76, any further sliding in the distal direction is prevented. Likewise, once implant 20 slides proximally until second stop 94 contacts prong 76, any further sliding in the proximal direction is prevented. Thus, first and second stops 92, 94 may be selectively spaced apart along longitudinal axis 30 to provide for a desirable amount of sliding between implant 20 and intramedullary nail 22, such as to provide for compression between the two fractured bone fragments. For example, limited sliding may be desirable during implantation, to compress a fractured femur head toward the trochanteric region. Additionally, limited motion may also stimulate bone growth and fracture healing during service. One of ordinary skill in the art will know and appreciate that first engagement surface 86 and second engagement surface 90 are not limited to the substantially flat configurations shown herein. Rather, first and second engagement surfaces 86, 90 may have any geometries that, when located adjacent one another, prevent rotation of implant 20 about axis 30, yet provide for sliding of implant 20 along longitudinal axis 30.

Figure 12A:
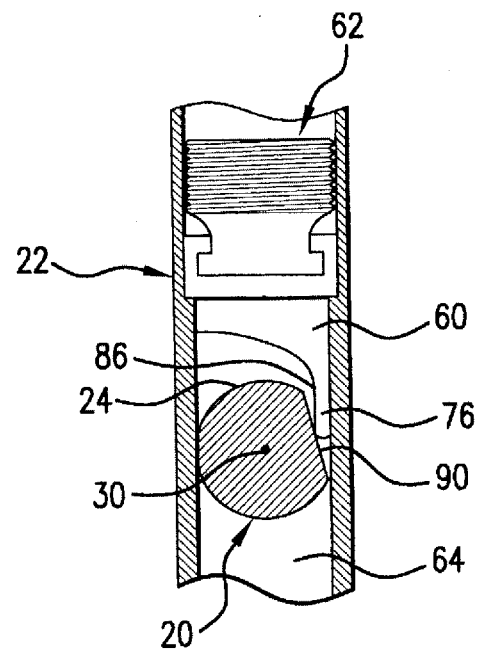
FIG. 12A is a partial cross-sectional view of the coupling mechanism of FIG. 5.
Figure 12B:
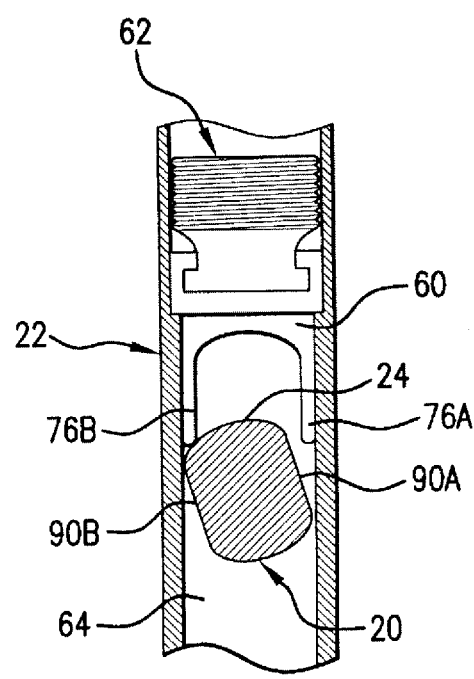
FIG. 12B is a partial cross-sectional view of an alternative embodiment of the coupling mechanism of FIG. 5, including a two-pronged body member.

As discussed above, body member 60 may have two or more prongs 76, and implant 20 may have two or more engagement surfaces 90. While multiple prongs may be desirable in certain applications (such as where extraordinarily large forces tend to rotate first implant 20 about its longitudinal axis 30 with respect to second implant 22), the exemplary embodiment having a single prong 76, shown in FIGS. 8-10, or alternatively having one prong longer than the other, provides for increased ease of assembly over the two-pronged or multi-pronged embodiments having equal length prongs. For example, a single prong 76, or one prong longer than the other, may be advantageous in the instance shown in FIG. 12A, where implant 20 is misaligned in bore 66 such that first engagement surface 86 is misaligned with second engagement surface 90. In this instance, movement of body member 60 toward implant 20 causes prong 76 to slide along second engagement surface 90 to influence implant 20 to rotate about longitudinal axis 30 until first and second engagement surfaces 86, 90 are flush with one another, and moreover, are engaged to substantially prevent rotation of implant 20. To the contrary, when a two-pronged embodiment having equal length prongs, as shown in FIG. 12B, is moved toward an implant 20 that is misaligned in bore 66, one of the prongs 76 contacts shaft 24 and prevents the other prong 76 from contacting the respective second engagement surface 90 to rotate implant 20 into alignment. As shown, second prong 76b is in contact with shaft 24 and prevents first prong 76a from contacting second engagement surface 90a to rotate implant 20 into proper alignment with body member 60. Thus, a single-pronged embodiment (or a multi-pronged embodiment having one prong longer than the other) may provide for increased ease of assembly of the coupling mechanism.

Referring back to FIGS. 7, 8 and 11, tabs 85, if provided, cooperate with grooves 65 to substantially prevent body member 60 from rotating within channel 64 of intramedullary nail 22. This provides the advantage of aligning prong(s) 76 with engagement surface(s) 90 in channel 64; thus, implant 20 can easily be inserted into bore 66 without requiring the surgeon to address the alignment of prong(s) 76.

Figure 13:
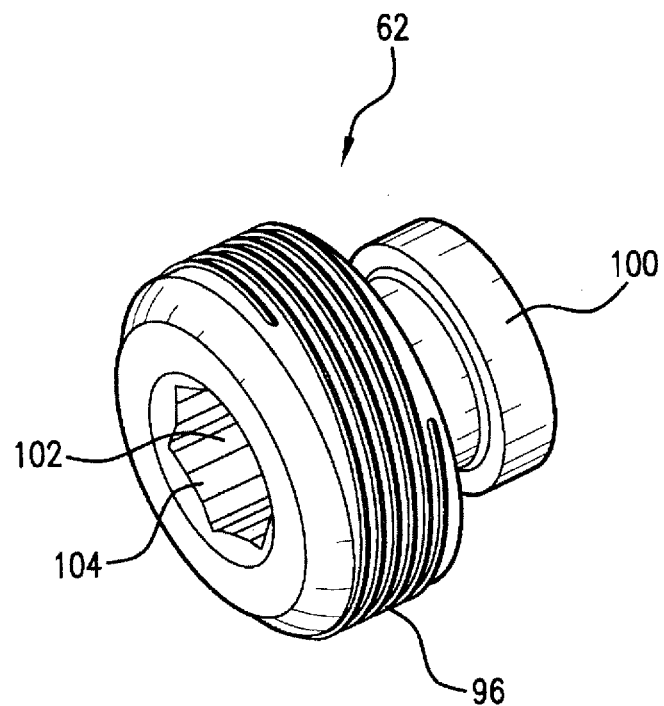
FIG. 13 is a perspective view of a drive member of the coupling mechanism of FIG. 5.
Figure 14:
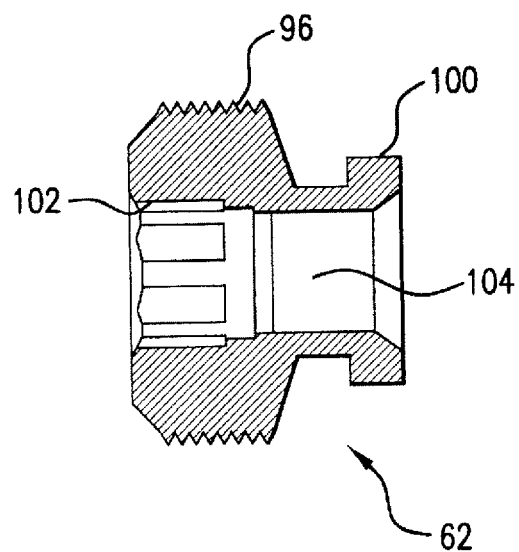
FIG. 14 is a cross-sectional view of the drive member of FIG. 13.

Referring to FIGS. 13 and 14, drive member 62 is shown in detail. Drive member 62 is configured and dimensioned to engage channel 64 to selectively hold body member 60 in position. In the exemplary embodiment shown, drive member 62 includes a series of threads 96 which mate with a series of threads 98 formed in channel 64, however other structures for securing drive member 62 in channel 64, such as springs or elastomers, are also within the present invention. Drive member 62 also includes an attachment portion 100 which is configured and dimensioned to rotatably couple drive member 62 to body member 60, such that drive member 62 may freely rotate with respect to body member 60. This is especially useful in the case where tabs 85 (FIGS. 8 and 11) cooperate with grooves 65 (FIG. 7) to prevent rotation of body member 60 in channel 64. In the exemplary embodiment shown, attachment portion 100 is a substantially disc-shaped flange that may be received between the channels 83a formed in arms 83 of body member 60. One of ordinary skill in the art will know and appreciate that any number of structures may alternatively be provided to couple drive member 62 to body member 60 and provide for rotation between the two parts, such as, for example, screws, swivels, pins, etc. One of ordinary skill in the art will also know and appreciate that body member 60 and drive member 62 may be either permanently attached, or detachably coupled to one another. Drive member 62 may also include a tool-engaging portion 102. As shown, drive member 62 defines a substantially hex-shaped opening 102 that is dimensioned and configured to engage a hex key. Tool-engaging portion 102 may alternatively be dimensioned and configured to engage any number of driving tools known to one of ordinary skill in the art, such as a screw driver or wrench. A cannulation 104 may optionally extend substantially axially through drive member 62 to permit insertion of a guide wire (not shown) therethrough.

Figure 15:
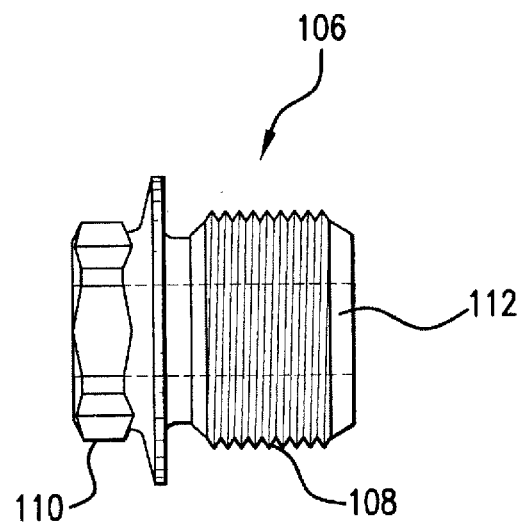
FIG. 15 is right side view of an end cap of the second implant of FIG. 6.
Figure 16:
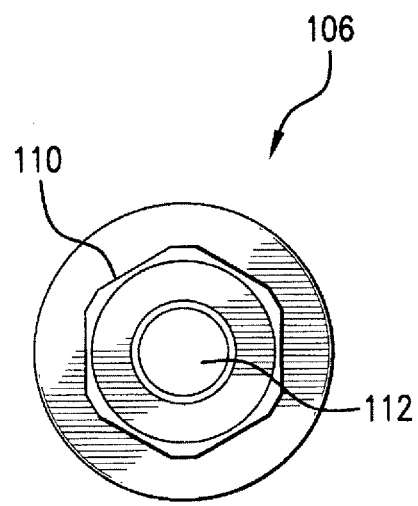
FIG. 16 is a back view of the end cap of FIG. 15.

Referring to FIGS. 15 and 16, an optional end cap 106 is shown. End cap 106, if provided, may be removably attached to the end of intramedullary nail 22 to conceal body member 60 and drive member 62 in channel 64. In addition, in the case where the surgeon chooses not to engage the locking mechanism (e.g., does not tighten drive member 62 in channel 64 in order to engage body member 60 with implant 20), end cap 106 may be urged against drive member 62 to prevent drive member 62, and consequently body member 60, from unintentionally migrating within channel 64.

In the illustrative embodiment shown in FIGS. 15 and 16, end cap 106 includes a series of threads 108 disposed thereon, which mate with the series of threads 98 formed on channel 64, or another series of threads formed on channel 64, to secure end cap 106 on intramedullary nail 22. Any number of structures known to one of ordinary skill in the art, including snap fasteners, adhesives or screws may alternatively be used to removably attach end cap 106 to intramedullary nail 22. End cap 106 may further include a tool-engaging portion 110, shown as a substantially hex-shaped portion 110 that is dimensioned and configured to engage a wrench. Tool-engaging portion 110 may alternatively be dimensioned and configured to engage any number of driving tools known to one of ordinary skill in the art, such as a hex-key or screw driver. A cannulation 112 may optionally be provided, which extends substantially axially through end cap 106 to permit insertion of a guide wire (not shown) therethrough.

Intramedullary nail 22 may be provided with body member 60, drive member 62 and, optionally, end cap 106 preassembled into channel 64, thus reducing the amount of time associated with implanting intramedullary nail 22, as well as reducing the amount of parts that must be handled by the surgeon. In the case where these components are preassembled, cannulations 72, 84, 104, and 112 (provided in intramedullary nail 22, body member 60, drive member 62, and cap 106, respectively) may be substantially aligned to permit insertion of a guide wire (not shown) completely through the preassembled unit. Thus, a guide wire may be used to guide intramedullary nail 22, including the preassembled locking components, into the intramedullary canal of a fractured bone.

Figure 17:
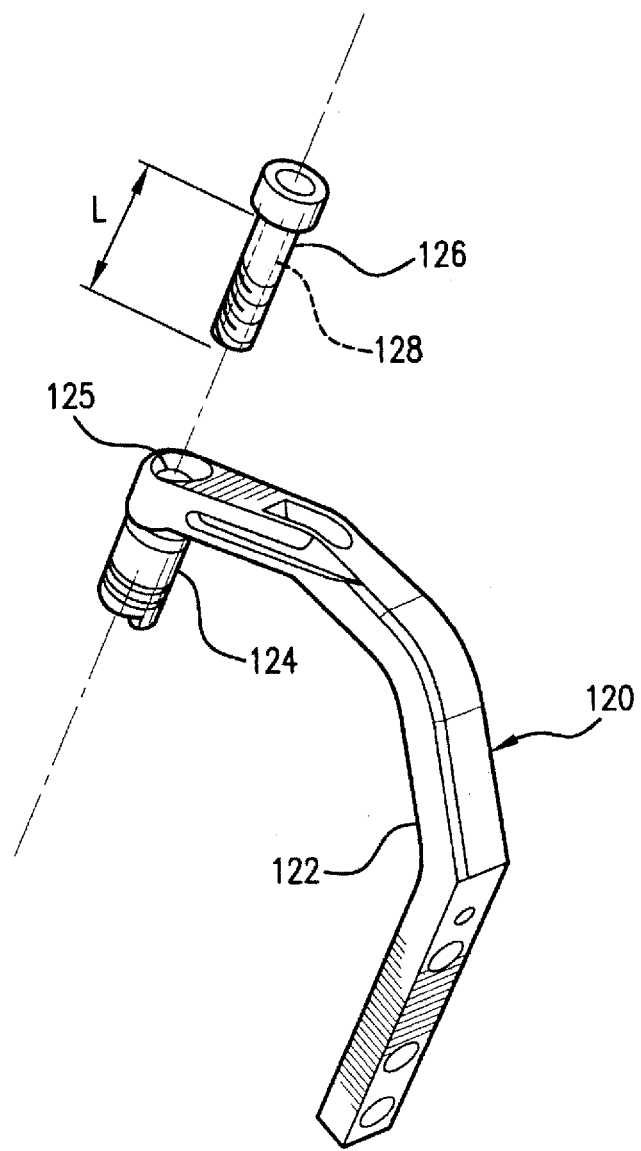
FIG. 17 is a perspective view of an illustrative embodiment of an insertion handle for use with an implant system according to the present invention.
Figure 18:
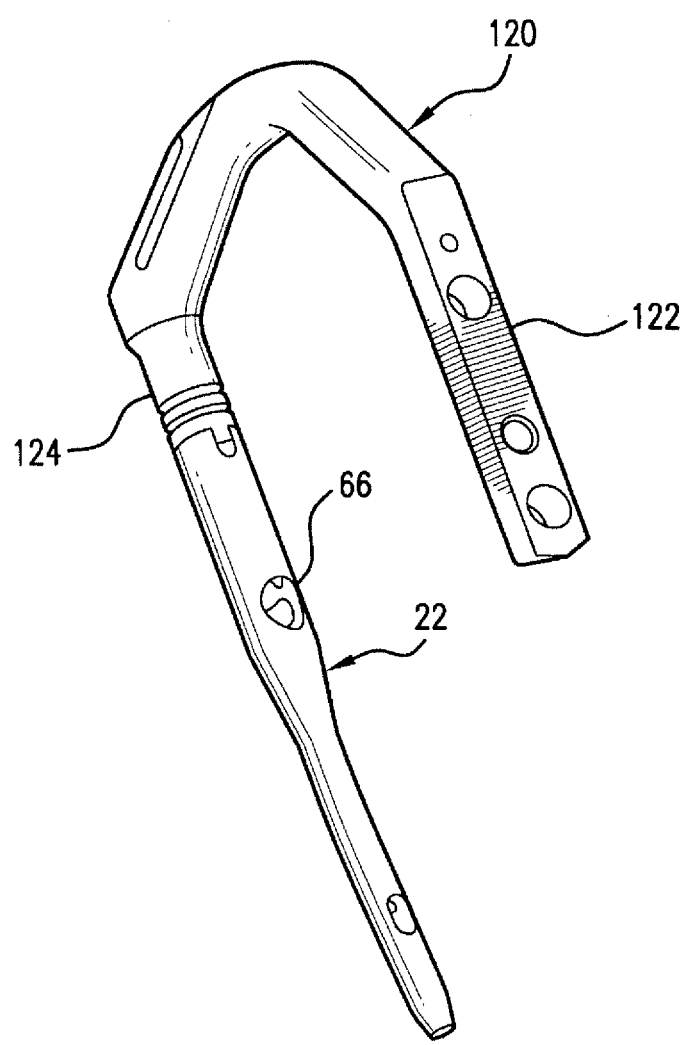
FIG. 18 is a perspective view of the insertion handle of FIG. 17, shown coupled to the second implant of FIG. 6.

As shown in FIGS. 17 and 18, an insertion handle 120 may optionally be provided to aid with insertion of the second implant (e.g., intramedullary nail 22). As shown, insertion handle 120 includes a handle portion 122 and a coupling portion 124. Coupling portion 124 may include a bore 125 that is dimensioned and configured to receive a coupling screw 126. Coupling screw 126 may be inserted through bore 125 and threaded into threads 98 of channel 64, to detachably couple insertion handle 120 to intramedullary nail 22. One of ordinary skill in the art will know and appreciate, however, that other structures may be employed to detachably couple insertion handle 120 to intramedullary nail 22. When attached to intramedullary nail 22, insertion handle 120 may be used to aid insertion of intramedullary nail 22 into the intramedullary canal. A cannulation 128 may optionally be provided in coupling screw 126 and aligned with cannulations 72, 84, and 104 (discussed above), to permit use of insertion handle 120 to insert intramedullary nail 22 over a guide wire. Furthermore, the length L of coupling screw 126, shown in FIG. 17, may be selected such that insertion handle 120 may be coupled to intramedullary nail 22 with body member 60 and drive member 62 preassembled therein.

While preferred embodiments and features of the bone implant and coupling mechanism have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed:

1. A method for treating at least one bone fracture, comprising the steps of:
(a) providing a first fracture fixation implant and a second fracture fixation implant wherein the first fracture fixation implant comprises a shaft having a proximal end and a distal end, the shaft defining a longitudinal axis between the proximal end and the distal end, a plurality of blades being disposed on at least a distal bladed portion of the shaft and helically twisted about the longitudinal axis, a non-bladed portion of the shaft extending proximally from the bladed portion, the non-bladed portion including a tapered region having a diameter that decreases in a direction toward the bladed portion and a substantially flat engagement surface configured and dimensioned to be engaged by a prong of a body member, the first fracture fixation implant including a distal and proximal stop surfaces at distal and proximal ends, respectively, of the flat engagement surface, wherein the second fracture fixation implant comprises a bore configured to receive the first fracture fixation implant;

(b) positioning the second fracture fixation implant in relation to a first bone fracture; and (c) inserting the first fracture fixation implant through the bore of the second fracture fixation implant so that at least a part of the non-bladed portion extends on a distal side of the second fracture fixation implant, the first fracture fixation implant being allowed to slide within the bore, wherein engagement of the prong with the substantially flat engagement surface prevents rotation of the first fracture fixation implant and wherein engagement of the prong with the distal and proximal stop surfaces defines a permitted range of sliding motion of the first fracture fixation implant within the second fracture fixation implant when the first fixation implant is in a final installed position therewithin.

2. The method of claim 1, wherein the bore is associated with the body member and a drive member that cooperate to substantially prevent rotation of the first fracture fixation implant within the bore.

3. The method of claim 1, wherein the drive member comprises a tool-engaging portion.

4. The method of claim 1, wherein at least one of the blades of the first fracture fixation implant has a variable blade width that varies in a direction along the longitudinal axis.

5. The method of claim 1, wherein step (b) includes inserting the second fracture fixation implant into an intramedullary canal.

6. The method of claim 5, wherein at least one of the first fracture fixation implant and the second fracture fixation implant is inserted by use of a driving tool.

7. The method of claim 1, wherein at least one bone fracture is located along a femur.

8. The method of claim 7, wherein at least one bone fracture is an intertrochanteric fracture.

9. The method of claim 1, wherein the second fracture fixation device further comprising at least one fixation hole, and further comprising the step of inserting at least one fastener into at least one fixation hole of the second fracture fixation device.

10. The method of claim 1, wherein the second fracture fixation device is substantially cannulated.

11. The method of claim 1, wherein step (b) includes using a guide to position the second fracture fixation implant.

12. The method of claim 1, wherein step (b) includes using an insertion handle to position the second fracture fixation implant.

13. The method of claim 12, wherein the insertion handle comprises a handle portion and a coupling portion, the coupling portion coupling the second fracture fixation implant to the insertion handle.

14. A method of treating at least one fracture of the femur comprising the steps of:

(a) providing a fixation implant and an intramedullary rod, wherein the fixation implant comprises:

a shaft having a proximal end and a distal end, comprising a distal bladed portion and a proximal non-bladed portion, the bladed portion and the non-bladed portion each having an outer diameter, wherein the shaft defines a longitudinal axis between the proximal end and the distal end; and a plurality of blades disposed on the bladed portion of the shaft helically twisted about the longitudinal axis, wherein the non-bladed portion includes a tapered region located substantially adjacent the bladed portion and a substantially flat engagement surface configured and dimensioned to be engaged by a prong of a body member, the fixation implant including distal and proximal stop surfaces at distal and proximal ends, respectively, of the flat engagement surface, wherein the tapered portion defines a tapered region diameter that decreases in a direction toward the bladed portion, and wherein the intramedullary rod comprises a head portion and a shaft portion, the head portion includes a bore configured to receive the fixation implant;

(b) inserting the intramedullary rod into the intramedullary canal of the femur; and (c) inserting the fixation implant through the bore of the intramedullary rod, such that the fixation implant engages a head of the femur and at least a portion of the non-bladed portion extends on a distal side of the intramedullary rod, and wherein engagement of the prong with the substantially flat engagement surface prevents rotation of the fixation implant and wherein engagement between the prong and the distal and proximal stop surfaces defines a permitted range of sliding motion of the fixation implant within the intramedullary rod when the first fixation implant is in a final installed position therewithin.

15. The method of claim 14, wherein at least one of the blades of the fixation implant has a variable blade width that varies in a direction along the longitudinal axis.

16. The method of claim 14, wherein the fixation implant is allowed to slide a predetermined distance within the bore without being able to back-out of the bore.

17. The method of claim 14, wherein at least one fracture is an intertrochanteric fracture.

18. The method of claim 14, wherein the stem portion of the intramedullary rod includes at least one fixation hole, and further comprising the step of inserting at least one fastener into at least one fixation hole of the intramedullary rod.

19. The method of claim 14, wherein the intramedullary rod is substantially cannulated.

20. The method of claim 14, wherein step (c) includes using a driving tool to insert the fixation implant through the bore and into the head of the femur.

21. The method of claim 14, wherein impact driving is employed to drive the plurality of blades into the head of the femur.

22. The method of claim 1, wherein the non-bladed portion of the first fracture implant mates with the bore of the second fracture fixation implant to provide a stable sliding interconnection between the non-bladed portion and the bore.

23. The method of claim 1, wherein the maximum outer diameter of the bladed portion is equal to or smaller than the maximum outer diameter of the non-bladed portion.

24. The method of claim 14, wherein the maximum outer diameter of the bladed portion is equal to or smaller than the maximum outer diameter of the non-bladed portion.

25. The method of claim 14, wherein the bore of the head portion is associated with the body member and a drive member.

* * * * *